(12) United States Patent
Ziaimehr

(10) Patent No.: US 8,470,011 B2
(45) Date of Patent: Jun. 25, 2013

(54) FORCED AIR WARMING UNIT

(75) Inventor: Allen Hamid Ziaimehr, Arden Hills, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

(21) Appl. No.: 13/134,233

(22) Filed: Jun. 2, 2011

(65) Prior Publication Data

US 2011/0301674 A1 Dec. 8, 2011

Related U.S. Application Data

(62) Division of application No. 11/704,547, filed on Feb. 9, 2007, now Pat. No. 7,976,572.

(51) Int. Cl.
*A61F 7/00* (2006.01)
*A61F 7/08* (2006.01)

(52) U.S. Cl.
USPC .......................................... 607/104; 607/107

(58) Field of Classification Search
USPC ................................. 607/104, 107
See application file for complete search history.

(56) References Cited

U.S. PATENT DOCUMENTS

| | | | |
|---|---|---|---|
| 3,724,092 A | 4/1973 | McCleerey | 34/99 |
| 3,778,851 A | 12/1973 | Howorth | 5/347 |
| 4,057,861 A | 11/1977 | Howorth | 5/365 |
| 4,225,775 A | 9/1980 | Carter | 392/383 |
| 4,321,456 A | 3/1982 | Ohnmacht et al. | 392/379 |
| 4,701,595 A | 10/1987 | Okutsu | 392/385 |
| 4,777,802 A | 10/1988 | Feher | 62/3.3 |
| 5,243,682 A | 9/1993 | Eberts | 392/370 |
| 5,300,098 A | 4/1994 | Philipot | 607/96 |
| 5,349,161 A | 9/1994 | Bockholt | 219/385 |
| 5,386,644 A | 2/1995 | Lawall et al. | 34/90 |
| 5,620,482 A | 4/1997 | Augustine et al. | 607/107 |
| 5,800,489 A | 9/1998 | Augustine et al. | 607/107 |
| 5,875,562 A | 3/1999 | Fogarty | 34/97 |
| 6,126,681 A | 10/2000 | Van Duren et al. | 607/96 |
| 6,210,428 B1 | 4/2001 | Augustine et al. | 607/107 |
| 6,230,501 B1 | 5/2001 | Bailey et al. | 62/51.1 |
| 6,447,538 B1 | 9/2002 | Van Duren et al. | 607/96 |
| 6,524,332 B1 | 2/2003 | Augustine et al. | 607/107 |
| D485,338 S | 1/2004 | Augustine et al. | D22/332 |
| 6,685,731 B2 | 2/2004 | Kushnir et al. | 607/104 |

(Continued)

FOREIGN PATENT DOCUMENTS

| | | |
|---|---|---|
| JP | 58142136 | 8/1983 |
| WO | WO 2008/097285 | 8/2008 |

OTHER PUBLICATIONS

P.O. Fanger, Thermal Comfort: Analysis and Applications in Environmental Engineering, Danish Technical Press, 1970, pp. 5-67.

(Continued)

*Primary Examiner* — Linda Dvorak
*Assistant Examiner* — Kaitlyn Smith
(74) *Attorney, Agent, or Firm* — X. Christina Huang; Adam M. Brammwell; Terrance A. Meador

(57) ABSTRACT

Both the flow rate and the temperature of the air exiting a forced air warming unit are regulated in response to a single act or operation of a single element of control on a manually-operated remote control.

8 Claims, 10 Drawing Sheets

U.S. PATENT DOCUMENTS

| | | | |
|---|---|---|---|
| 6,711,767 B2* | 3/2004 | Klamm | 5/423 |
| 6,840,955 B2 | 1/2005 | Ein | 7/108 |
| 6,876,884 B2* | 4/2005 | Hansen et al. | 607/98 |
| 7,014,431 B2* | 3/2006 | Hansen et al. | 417/313 |
| 7,090,692 B1 | 8/2006 | Augustine et al. | 607/107 |
| 6,210,428 C1 | 11/2008 | Augustine et al. | 607/107 |
| 7,497,870 B2 | 3/2009 | Frey et al. | 607/107 |
| 7,749,261 B2 | 7/2010 | Hansen et al. | 607/107 |
| 2002/0144343 A1 | 10/2002 | Kuiper et al. | 5/81.1 R |
| 2003/0045918 A1 | 3/2003 | Turner et al. | 607/107 |
| 2003/0114903 A1* | 6/2003 | Ellingboe | 607/104 |
| 2004/0107717 A1* | 6/2004 | Yoon et al. | 62/230 |
| 2004/0153132 A1 | 8/2004 | Cobb et al. | 607/107 |
| 2004/0204748 A1* | 10/2004 | Hansen et al. | 607/104 |
| 2005/0070979 A1* | 3/2005 | Hansen et al. | 607/104 |
| 2005/0143796 A1 | 6/2005 | Augustine et al. | 607/104 |
| 2006/0190065 A1* | 8/2006 | Frey et al. | 607/104 |
| 2006/0212102 A1 | 9/2006 | Frey et al. | 607/104 |
| 2006/0260609 A1 | 11/2006 | Bruening | 128/200.24 |
| 2008/0195184 A1* | 8/2008 | Ziaimehr | 607/104 |
| 2012/0144848 A1* | 6/2012 | Yeo et al. | 62/56 |

OTHER PUBLICATIONS

C.B. Mahony & J. Odom, Maintaining intraoperative normothermia: A meta-analysis of outcomes with costs. *AANA Journal*. Apr. 1999. v. 67, No. 2:155-164.

Author Unknown, The Howarth Surgicare Microclimator® and Intensive Care Mattress, Howarth Air Conditioning Limited, Surgicare Division, date unknown, 2 pages.

Wedley, Jr., Studies of Temperature Balance After Open-Heart Surgery, *Critical Care Medicine*, vol. 3, No. 4, Jul.-Aug. 1975, pp. 134-138.

H.E. Howarth, The Howarth Low Air Loss Mattress and Climators, Howarth Surgicare, date unknown, 7 pages.

Request for Reexamination by Patent Owner Pursuant to 37 CFR § 1.510 in US Patent 6,210,428, mailed Feb. 15, 2002.

BPAI Decision on Appeal, Appeal 2008-0589, Reexamination Control No. 90/006,221, Patent 6,210,428, Decided Apr. 24, 2008.

International Preliminary Report on Patentability, PCT/US2007/021551, mailed Aug. 20, 2009.

* cited by examiner

FORCED AIR WARMING UNIT

PRIORITY AND RELATED APPLICATIONS

This patent application is a divisional of U.S. application Ser. No. 11/704,547, filed Feb. 9, 2007, now U.S. Pat. No. 7,976,572, issued Jul. 12, 2011.

This patent application contains subject matter related to the following patent applications, which are incorporated herein by this reference:

U.S. application Ser. No. 11/363,136 filed Feb. 27, 2006, now U.S. Pat. No. 7,749,261, which is a continuation of U.S. patent application Ser. No. 10/989,135 filed Nov. 15, 2004, now U.S. Pat. No. 7,014,431, which is a continuation of U.S. patent application Ser. No. 10/411,431 filed Apr. 10, 2003, now U.S. Pat. No. 6,876,884;

U.S. application Ser. No. 10/508,319, for "Patent Comfort Apparatus And System," filed Sep. 20, 2004 as the US national phase of PCT/US2003/11128, and published on Jun. 30, 2005 under Publication No. 2005/0143796;

U.S. patent application Ser. No. 10/895,672, filed Jul. 21, 2004, entitled "Perioperative Warming Device", now abandoned, published on Jan. 20, 2005 under Publication No. 2005/0015127;

U.S. patent application Ser. No. 11/005,883, filed Dec. 7, 2004, entitled "Warming Device with Varied Permeability" and published on Jun. 8, 2006 under Publication No. 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. 2006/0122672, now U.S. Pat. No. 7,364,584;

U.S. patent application Ser. No. 11/057,396, filed Feb. 11, 2005, entitled "Perioperative Warming Device" and published on Aug. 7, 2006 under Publication No. US 2006/0184215, now U.S. Pat. No. 7,276,076; and, U.S. patent application Ser. No. 11/583,432, filed Oct. 19, 2006, entitled "Multifunction Warming Device for Perioperative Use", published on Apr. 26, 2007 under publication No. 2007/0093882 A1, now U.S. Pat. No. 7,819,911.

BACKGROUND

This specification relates generally to thermal comfort and more particularly to a system for providing pressurized, thermally conditioned air to a convective device under manual remote control. Another aspect concerns the control of a forced air warming unit by regulation of both the flow rate and the temperature of the air exiting the forced air warming unit in response to a single manual act or manual operation of a single element of control.

It is known to use therapeutic warming to treat patients perioperatively for hypothermia in order to mitigate the risk of adverse outcomes such as increased rates of wound infection, lengthened hospital stays, and increased mortality rates. Hypothermia occurs when the core body temperature falls below 36° C.; mild hypothermia occurs when core body temperature is in the range of 34° C. to 36° C. The clinical effectiveness of therapeutic warming depends upon delivery of enough heat to a patient to raise the patient's core body temperature to, or maintain it within, a narrow range, typically near 37° C. This range is called "normothermic" and a body with a core temperature in this range is at "normothermia".

Therapeutic warming is contrasted with "comfort warming" which is intended to maintain or enhance a patient's sense of "thermal comfort". Of course, therapeutic warming may also comfort a patient by alleviating shivering, for example, but this is a secondary or ancillary effect. Thermal comfort is a subjective notion; however, the environmental conditions necessary to produce a sense of thermal comfort in a population of human beings are known and well tabulated. See, for example, P. O. Fanger, THERMAL COMFORT: Analysis and Applications in Environmental Engineering, Danish Technical Press, 1970, pp. 5-67. Fanger defines thermal comfort as "that condition of mind which expresses satisfaction with the thermal environment." Even when a patient is normothermic, less than ideal environmental conditions can result in acute feelings of thermal discomfort. Under normothermic conditions, thermal comfort is largely determined with reference to skin temperature, not core body temperature.

Aside from humanitarian concerns, there are many good reasons to provide for the thermal comfort of a patient in a clinical setting. For example, attending to the thermal comfort of patients will reduce the time nurses spend responding to patients' requests for thermal comfort interventions. Lack of thermal comfort is a frequent complaint among patients, and results in poor patient ratings for clinics and hospitals. Ensuring the thermal comfort of patients will enhance patient satisfaction. Furthermore, the provision of means to enable a patient to selectively control the thermal characteristics of his or her own personal microenvironment in a clinical setting should produce the following additional unexpected benefits: 1.) reduced blood pressure providing easier entry to blood vessels for IV access; 2.) reduced pain sensation; 3.) normalizing of the patient's perception of time slowing; 4.) reduced anxiety and reduced need for medication. These and other objectives are realized when a patient is maintained in a state of thermal comfort. With comfort warming, it is also possible to slightly raise the core body temperature to store enough heat so that normal body heat loss during the course of a short operation will not lead to hypothermia.

Patient warming in a clinical environment may be provided by convective devices that receive and distribute warmed, pressurized air, inflate, and then expel the distributed air through one or more surfaces toward a patient. Examples of convective devices that deliver therapeutic warming are thermal blankets that are deployed over prone patients. See, for example the thermal blanket described in commonly-owned U.S. Pat. No. 7,090,692. Comfort warming may be provided by convective means such as the convectively operated warming devices described in commonly-owned international Publication No. WO 2003/086500, incorporated herein by reference. In fact, such warming devices may be constructed to be operated in a clinical mode, under control of health care personnel, to deliver therapeutic warming, and in a comfort mode, which may be controlled by the patient, to deliver comfort warming; see commonly-owned US Publication No. 2006/012267, also incorporated herein by reference.

The temperature requirements for thermal comfort are variable. They depend on the environment, and also on personal and subjective factors. As a result, people usually desire to have direct control over their own thermal environment. A convectively operated warming device according to the incorporated publications includes a clinical garment such as a hospital gown that forms a thermal microenvironment in the space between the garment and a patient's body. The warming device further includes an inflatable convective apparatus on an inside surface of the clinical garment that vents warmed air into the thermal microenvironment. In the incorporated U.S. Pat. Nos. 7,014,431 and 6,876,884, a forced-air warming unit is described which provides a warmed pressurized air stream for operation of the convective apparatus. The forced air warming unit includes a manually-operated remote control that enables a patient to vary air stream temperature.

A thermal microenvironment should suit an individual's notion of thermal comfort to the fullest extent possible. The ability to vary air temperature alone affords only a gross control over the thermal microenvironment. In order to meet a patient's subjective standard of thermal comfort, it is desirable for the patient to have control over more than one factor contributing to the thermal microenvironment. In this regard, control of the air flow rate and control over the temperature of an air stream would enable more sensitive adjustment of the thermal characteristics of the microenvironment. It would be possible to adapt forced air warming unit designs for finer, more sensitive control by provision of separate blower speed and temperature controls, but dual-control operation may be confusing to the patient and may lead to more anxiety and discomfort through a perceived loss of effect because of unpredictable results. In the manual control apparatus and method to be described, an individual is afforded a simple, unambiguous way to control both air flow rate and air temperature in a stream of air emitted by a forced air warming unit by means of a single manually-operated control element.

SUMMARY

A forced air warming system includes a remotely-controlled forced air warming unit to be used with a heat applicator including a convective device and a hose for connecting the forced air warming unit with the convective device.

A manually-operated remote control apparatus for use by an individual to maintain thermal comfort in a microenvironment controls a forced air warming unit as it pressurizes and heats air for delivery to a convective device that convectively warms the microenvironment.

A manually-operated remote control apparatus enables a user to adjust the output temperature and flow rate of a stream of air provided by a forced air warming unit. The apparatus may also enable the patient to turn the unit on or off. Control of both air temperature and air flow rate in response to a single act of the patient is preferred, and the control may be provided by a single manually-operated element on the remote control apparatus.

DETAILED DESCRIPTION OF THE EMBODIMENTS

In the incorporated U.S. Pat. No. 7,014,431 and U.S. Pat. No. 6,876,884, a remote control apparatus used with a forced air warming unit supports regulation of air stream temperature alone in order to adjust the thermal characteristics of a person's thermal microenvironment. The speed and efficacy with which the person can adjust the conditions of thermal comfort in response to changes in the microenvironment would be enhanced by providing a remote control apparatus enabling manual regulation by the person of air stream temperature and air flow velocity produced by a forced air warming unit. However, providing a remote control apparatus with separate temperature and air speed controls would require the patient to perform separate acts of control in order to adjust both the air stream temperature and the air stream flow rate, which may be confusing and perceived to be excessively complex and unresponsive, thereby leading to anxiety and discomfort.

Accordingly, this specification describes and illustrates a method, an apparatus, and a system for regulating both the temperature and the flow rate of the air stream in response to a single control action by a user. Preferably, the single control action may be performed using a single manually-operated element to regulate both air stream temperature and air stream flow rate.

Figure 1:
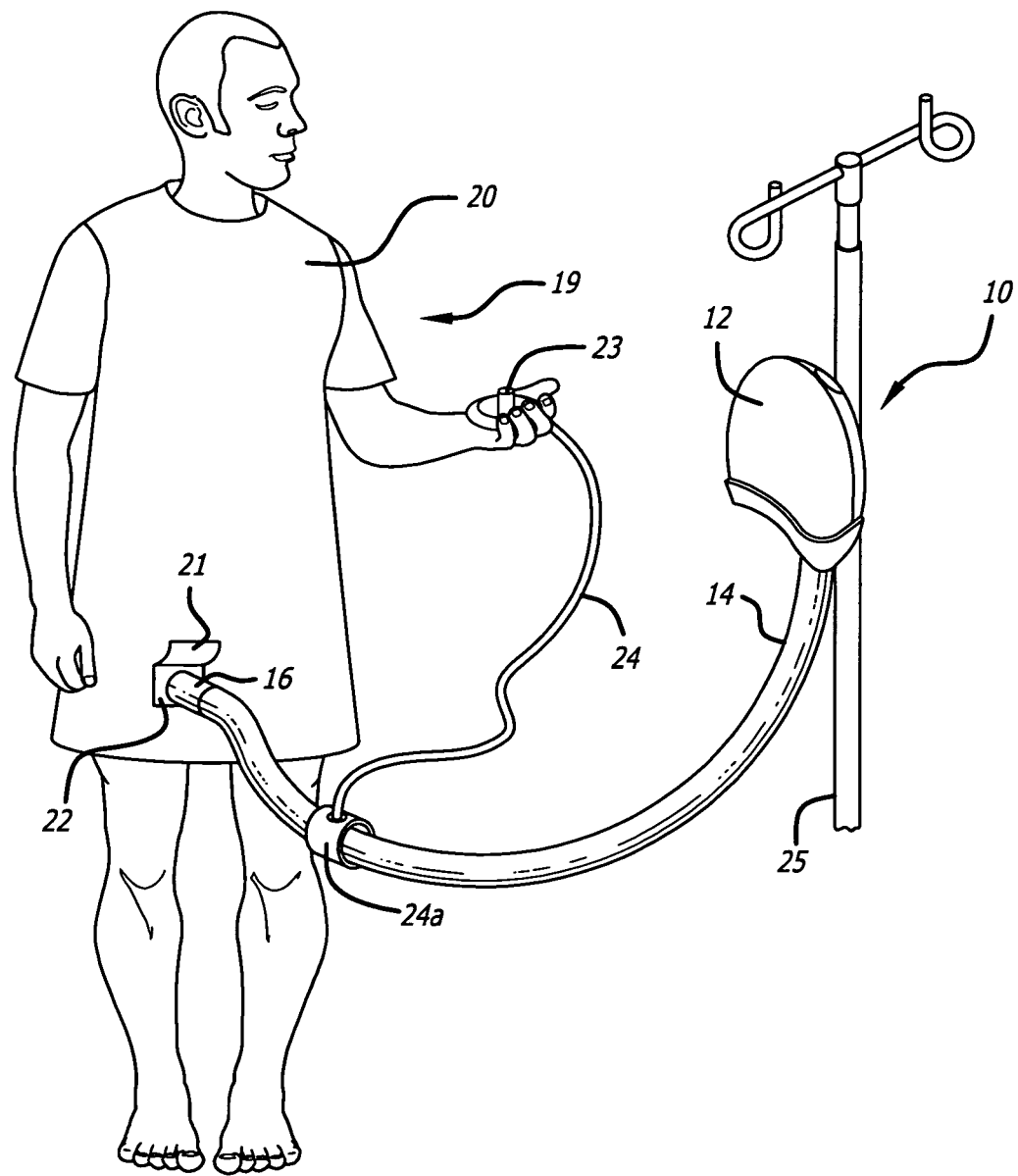
FIG. 1 shows a forced air warming unit in combination with a warming device.

FIG. 1 illustrates a convectively operated warming system such as may be deployed for use in a clinical setting to warm an individual. When convenient or useful for illustration, the individual may be referred to herein as a patient, a person, or a user. For example, the warming system may be used to provide comfort warming for the individual. In this regard, the warming system includes a forced air warming unit 10 for pressurizing and heating air in a casing 12. One end of an air hose 14 is connected to the casing 12, and the other end of the air hose 14 is connected by a nozzle or connector 16 to a convectively operated warming device 19. Without limitation of this disclosure, the patient warming device may be constructed as taught in the incorporated publications 2003/086500 and US 2006/012267. The patient warming device 19 is worn by a person who may be standing, sitting, or prone. The patient warming device 19 includes a clinical garment 20, such as a lightweight robe or hospital gown, which opens at the back or a side, is worn with an open bottom like a skirt or kilt, and is supported primarily at the shoulders and/or neck of the person. The patient warming device 19 also includes an inflatable convective apparatus (not shown) supported on an inside surface of the clinical garment 20. The inflatable convective apparatus includes at least one inflation port constructed to receive and retain the end of an air hose. In FIG. 1, a flap 21 in the clinical garment 20 provides access to one such inflation port 22, in which the nozzle or connector 16 is retained. In operation, the forced air warming unit 10 produces a stream of pressurized, heated air which exits the casing 12 at some air stream temperature (which may range, for example, from ambient to an elevated level) and some air stream velocity into the one end of the air hose 14. This air stream is conducted by the air hose 14 and into the inflatable convective apparatus through the inflation port 22. The inflatable convective apparatus receives the air stream, inflates, distributes the warmed, pressurized air within an inflatable structure, and emits the air through one or more permeable surfaces for convective transfer of heat to the body of the person wearing the clinical garment 20. The clinical garment 20 defines a microenvironment about the person. The forced air warming unit 10 may be adapted for mounting on an IV pole, as shown, or may be supported on a wall, a fixture, a table, or any other equivalent.

Examples of inflatable convective apparatuses used to provide one or more modes of warming, including comfort warming, are found in the incorporated publications. These inflatable convective apparatuses are supported on an inside surface of a clinical garment such as the garment 20 shown in FIG. 1 to form a patient warming apparatus such as the patient warming apparatus 19.

With further reference to FIG. 1, a manually-operated remote control 23 may be connected by signal cable 24 to control circuitry (not shown) disposed within the casing 12. Preferably, the remote control 23 enables the person wearing the patient warming device 19 to regulate the temperature and velocity of the stream of air produced by the forced air warming unit 10 and thereby to control factors affecting the thermal comfort of his or her personal microenvironment.

Figure 2:
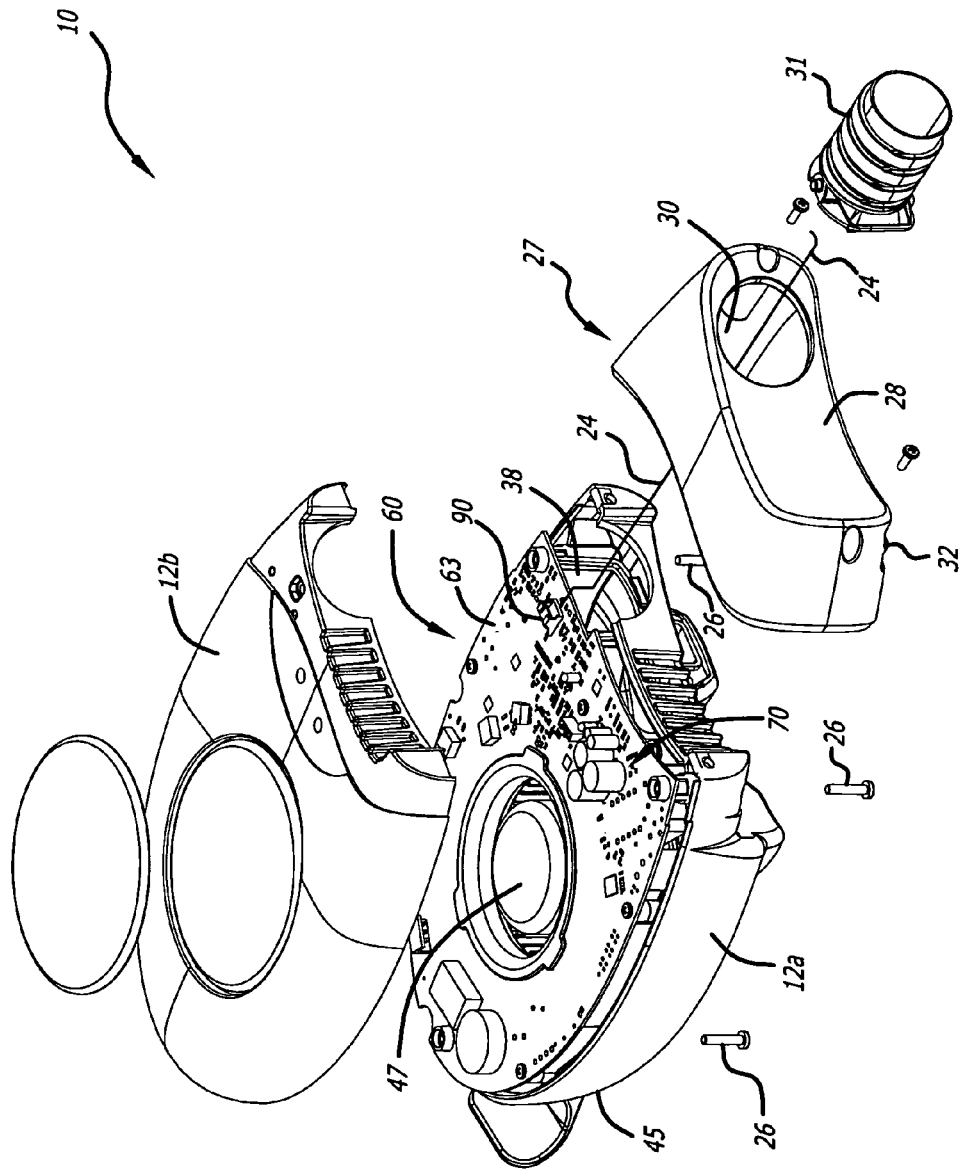
FIGS. 2 and 3 show perspective exploded views of an exemplary forced air warming unit.
Figure 3:
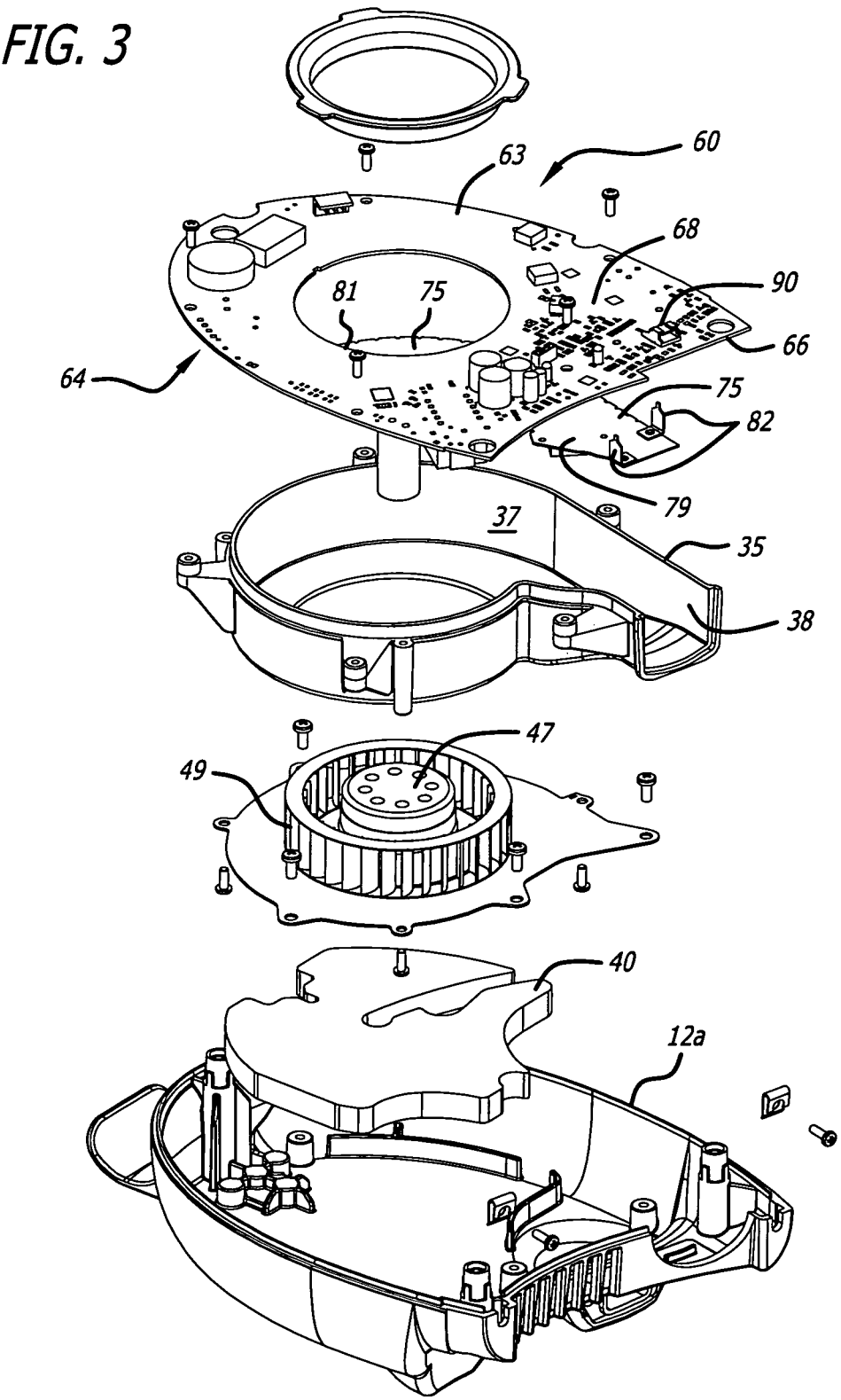

A representative forced air warming unit will now be described, not to limit the scope of this specification, but to afford a concrete example with which to understand and appreciate single action control of both flow rate and temperature of an air stream provided by a forced air warming unit in a context such as that shown in FIG. 1. In this regard, FIGS. 2 and 3 are perspective exploded views showing an illustrative arrangement of elements of the forced air warming unit 10. The unit 10 includes a casing 12 having first and second halves 12a and 12b that are joined by threaded screws 26. Grated intake openings 13 are provided in the front ends of the first and second halves 12a and 12b. A shaped end piece 27 defines an end face 28 of the casing 12 which fits over the front of the casing when the first and second halves 12a and 12b are joined. The end face 28 has an outlet opening 30 to which an adapter 31 is fitted for receiving and retaining the end 31 of an air hose. A grated intake opening 32 is provided on a bottom surface of the end piece 27. A scroll housing 35 with a curved inside surface 37 is secured in the casing half 12a. The scroll housing has an air diffusing outlet 38 positioned near the outlet opening.

In FIGS. 2 and 3, a motor mounting plate 40 is secured to the casing half 12a. A radial blower unit includes a motor 47 with an impeller 49 mounted thereto. Preferably, the motor 47 is a brushless DC motor. The radial blower unit is secured to the motor mounting plate 40, and positioned generally centrally in the scroll housing 35.

A circuit board 60 is supported by the scroll housing 35 and secured to the casing half 12a. The circuit board has a conventional multilayer construction with a first side 63 which faces the casing half 12b, a second side 64 facing and supported on the scroll housing 35, and a forward edge 66 disposed near or adjacent the intake opening 32. Control circuitry 68 for regulation of air stream velocity and temperature and a DC power supply 70 for the motor 47 are mounted by conventional solder technology on the first side 63, and power conversion circuitry is mounted on the second side 64.

Figure 4:
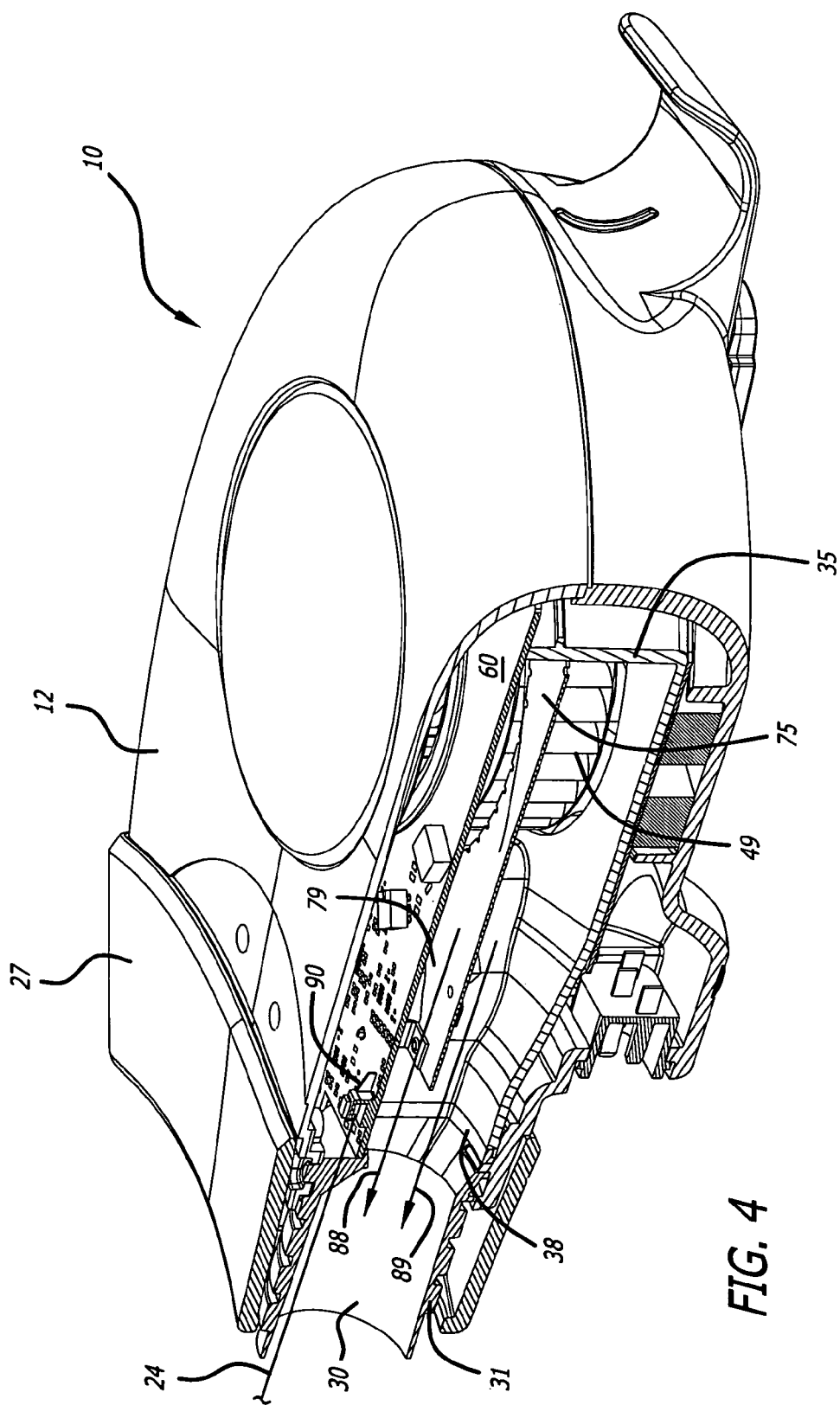
FIG. 4 is a partial sectional view showing details of the forced air warming unit.

Referring to FIGS. 2-4, a heater plate 75 is supported in the scroll housing 35, near the diffusing outlet 38. In some instances, the heater plate 75 may be constituted of an elongate, tapered, curved metal piece having a relatively wider first end 79 positioned near the diffusing outlet 38 and a relatively narrower second end 81 positioned in the scroll housing 35 between the impeller 49 of the radial blower unit and the curved inside surface 37 of the scroll housing. The heater plate 75 has standoffs 82 by which it is soldered to the second side 64 of the circuit board 60. As best seen in FIG. 4, the heater plate 75 is positioned between the circuit board 60 and the motor mounting plate 40. The heater plate 75 is wound with a thin metallic electrical conductor (not shown) which is connected to the control circuitry 68.

With reference to FIG. 4, the motor 47 is energized by provision of drive power from the DC power supply, causing the impeller 49 to rotate, which pressurizes and forces air in the scroll housing 35 to move against the curved inside surface toward and through the air diffusing outlet 38 into the end of the air hose 31. Movement of heated pressurized air into the air hose 31 is represented by the arrows 88 and 89. In response, air is drawn into the unit 10 through the intake opening 32 in the end piece and the intake openings 13. Control and temperature sensors providing sensor outputs to the control circuitry 68 may be located on the second side 64 of the circuit board in close proximity to the first end 79 of the heater plate 75, in the air diffusing outlet 38.

FIGS. 2-4 illustrate but one example of how the manually-operated remote control 23 may be coupled to the control circuitry 68, and the example is not meant to be limiting. In this example, the signal cable 24 runs between the remote control 23 and the control circuitry 68. Although not necessary, it is convenient for the signal cable 24 to penetrate into the interior of the air hose 14 through the coupling 24a. The cable 24 may have the capacity to transfer more than one control signal, and indeed may have more than one signal path. Inside the air hose, the signal cable 24 extends to and through the adapter 31, connecting to the control circuitry 68 through a plug 90 mounted on the first side 63 of the circuit board 60.

Figure 5:
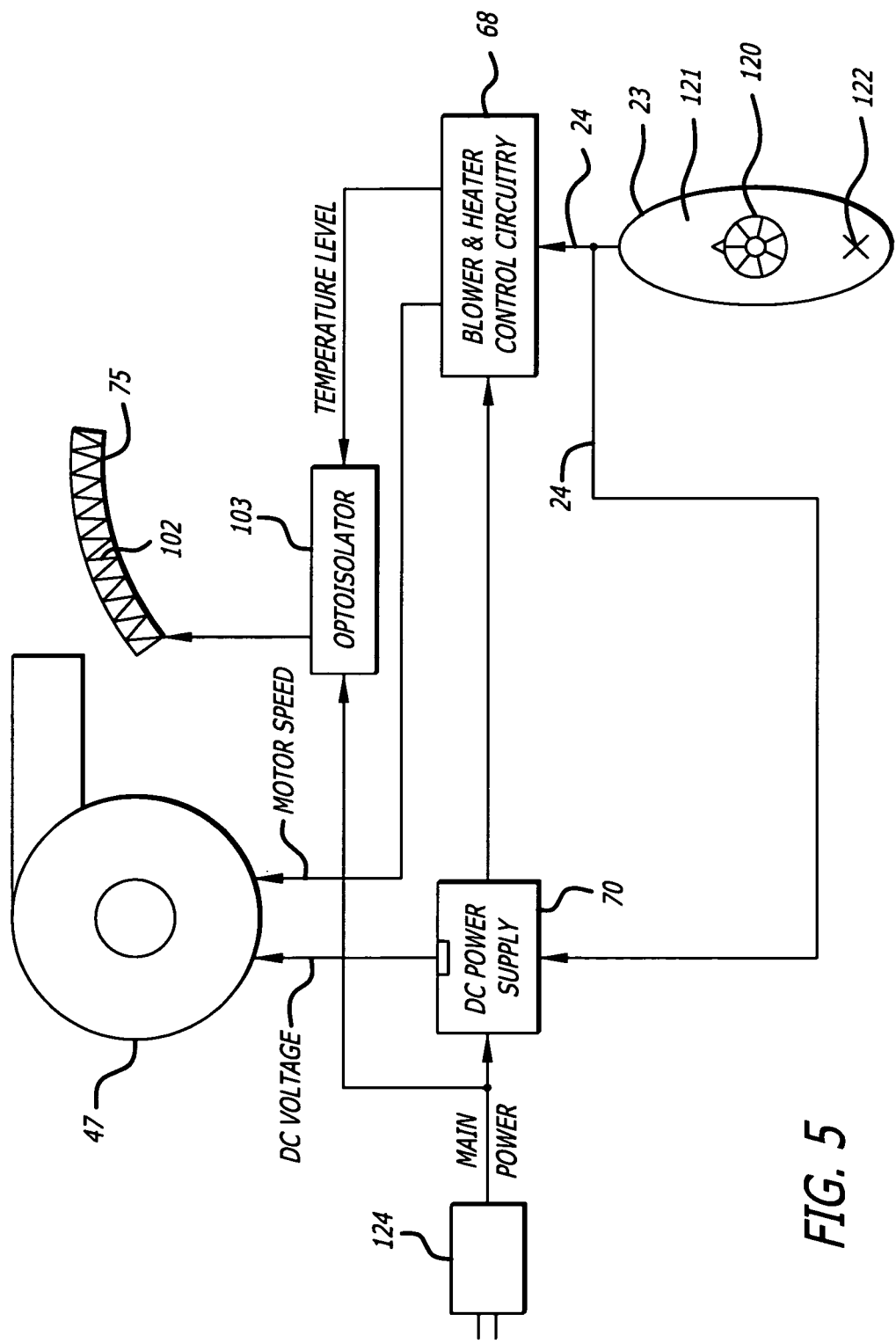
FIG. 5 is a schematic diagram illustrating control of forced air warming unit operation.

A block diagram of a scheme to control forced air warming unit operation is shown in FIG. 5. Presuming a forced air warming unit corresponding to the forced air warming unit 10 shown in FIGS. 2-4, the remote control 23 is adapted to include a control element 120 mounted at or on a control surface 121 of the remote control 23. The signal cable 24, which may comprise as many individual signal channels or conductors as necessary to implement the desired control functions, connects the remote control 23 to the electronics in the forced air warming unit. A plug 124 is shown in FIG. 5 for connecting electrical and electronic components in the forced air warming unit 10 to a main power source. The control element 120 is connected by one or more signal channels or conductors (such as wires) in the cable 24 to the control circuitry 68 for regulating both the velocity and the thermal condition of pressurized, heated air produced by the forced air warming unit 10. In some aspects, the same control element 120 may also be connected by other signal channels or conductors (such as wires) in the cable 24 to the DC power supply 70 to control an on/off function (indicated by the marking 122) of the motor 47 that is implemented via the supply 70. The control element 120 may be a manually-operated element. For example, the control element may be a hand-operated knob rotatably mounted at or on the control surface 121 and connected to one or more potentiometers in the remote control 23 that produce one or more continuously-variable control signals conducted to the control circuitry 68 through the signal cable 24. The magnitude of some characteristic (such as voltage or current) of one or more control signals produced by the remote control 23 causes the control circuitry 68 to set the speed of the motor 47 by a motor speed signal and to set the level of current through the windings 102 of the heater plate 75 by a temperature level signal. Variation of the position of the knob varies the magnitude of the one or more control signals, thus varying the speed of the motor and the level of the winding current. This permits a user to regulate, with a single control action, or by a single, manually-controlled element, the air stream flow rate or velocity V and air stream temperature T of the pressurized air that enters the user's microenvironment. The magnitude of some characteristic (such as voltage or current) of another control signal causes the DC power supply 70 to switch a DC voltage for the motor 47. When switched on, the DC voltage causes the motor 47 to rotate at a speed set by the motor speed signal. When switched off, the DC voltage causes the motor 47 to cease rotation.

Figure 6:
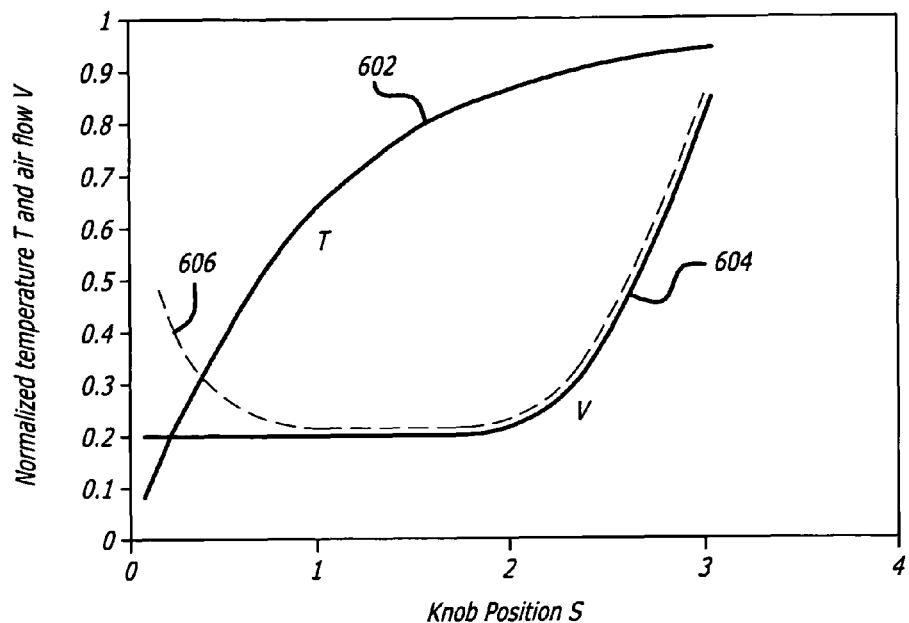
FIG. 6 is a chart showing temperature and flow rate control characteristics of a thermal comfort controller.

FIG. 6 is a chart showing an exemplary temperature control characteristic 602, a first exemplary monotonic flow rate control characteristic 604, and a second exemplary flow rate control characteristic 606 for a method directed to the single control action regulation of thermal comfort. The horizontal axis of chart represents the position in arbitrary units of a manually-operated control element (hereinafter, "control element"). For example, the control element may be a single control knob on the manually-operated remote control 23 shown in FIG. 5 connected to operate one or more potentiometers, or any other example described herein, or any equivalent thereof. A variable characteristic of the control element such as position may be considered to represent the value of at least one control signal S produced by the control element to regulate the temperature T and air flow velocity V of a warmed air stream produced by a warming unit. The vertical axis of the chart represents both the air stream temperature T (in degrees) normalized to a predetermined range (0.0-1.0) and air stream flow rate or velocity V (in cubic units per time) normalized to a predetermined range (0-100%).

As may be clearly appreciated from the chart of FIG. 6, the monotonic positive nonlinear slope $(\partial T/\partial S)$ of temperature control characteristic 602 means that the air stream temperature T increases responsive to increasing the control position signal S (in electrical units such as ohms, volts, or amperes) and the monotonic positive nonlinear slope $(\partial V/\partial S)$ of air flow control characteristic 604 means that the air stream flow rate V also increases responsive to the same increasing control position (signal) S. This nonlinear control of both temperature T and flow rate V by means of a simple manipulation of a single knob or similar patient-operated control element is preferred and eliminates possible patient confusion, serving to accelerate the effects of heating demands and decelerate the effects of cooling demands made by the patient when manipulating control 23. Such shaping of patient control demands results in improved perception of thermal comfort. This arrangement is not meant to be limiting, but is preferred for patient comfort in many circumstances.

An alternative air flow control characteristic 606 has a "bathtub" shape that both increases flow rate V responsive to demand for higher temperature T in an upper control range and increases flow rate V responsive to demand for lower temperature T in a lower control range. Such increased flow rate V at both extremes may be more useful in some ambient environments or with some patient conditions than the monotonic air flow control characteristic 604. Those versed in the art can readily appreciate that other control characteristics for the simultaneous control of air temperature T and air flow rate V may be easily implemented with reference to the following teachings, to meet other particular thermal comfort requirements.

Note in the chart of FIG. 6 that the temperature control characteristic 602 is shaped to reduce the rate of change $(\partial T/\partial S)$ of the temperature T with respect to control position (signal) S as the control position S increases. By using nonlinear exponential shaping, for example, temperature characteristic 602 may also be shaped to reduce the rate of change $\partial(\partial T/\partial S)/\partial S$ with respect to control signal S of the rate of change $(\partial T/\partial S)$ responsive to an increase in the control signal S. Conversely, air flow control characteristic 604 is shaped to increase the rate of change $(\partial V/\partial S)$ of flow rate V with respect to patient control position (signal) S as the control position S increases. Similarly, by using nonlinear exponential shaping, for example, air flow characteristic 604 may also be shaped to increase the rate of change $\partial(\partial V/\partial S)/\partial S$ with respect to the control signal S of the rate of change $(\partial V/\partial S)$ responsive to an increase in the control signal S. Finally, note that air flow control characteristic 606 is shaped to increase the rate of change $(\partial V/\partial S)$ of flow rate V with respect to patient control position (signal) S in an upper range of patient control positions and shaped to decrease the rate of change $(\partial V/\partial S)$ of flow rate V with respect to patient control position (signal) S in a lower range of patient control positions, for example, to improve thermal comfort in some circumstances.

FIG. 1 illustrates a representative operational environment for application of single-act and single-element control of temperature T and air flow velocity V produced by a forced air warming unit, according to the chart of FIG. 6. In this regard, a manually-operated remote control apparatus such as the manually-operated remote control of 23 preferably includes a single, manually-operated control element to generate at least one signal that controls, regulates, or adjusts both T and V simultaneously. In the discussion to follow, which is meant for illustration, the control element is illustrated by a rotatable knob connected to operate at least one potentiometer; rotation of the knob continuously varies the resistance of the potentiometer. Characteristics of a control signal produced by the potentiometer change in response the variation in resistance. Control circuitry responsive to the control signal causes the temperature and velocity of the air stream produced by the forced air warming unit 10 to vary in response to changes in control signal characteristics.

Figure 7:
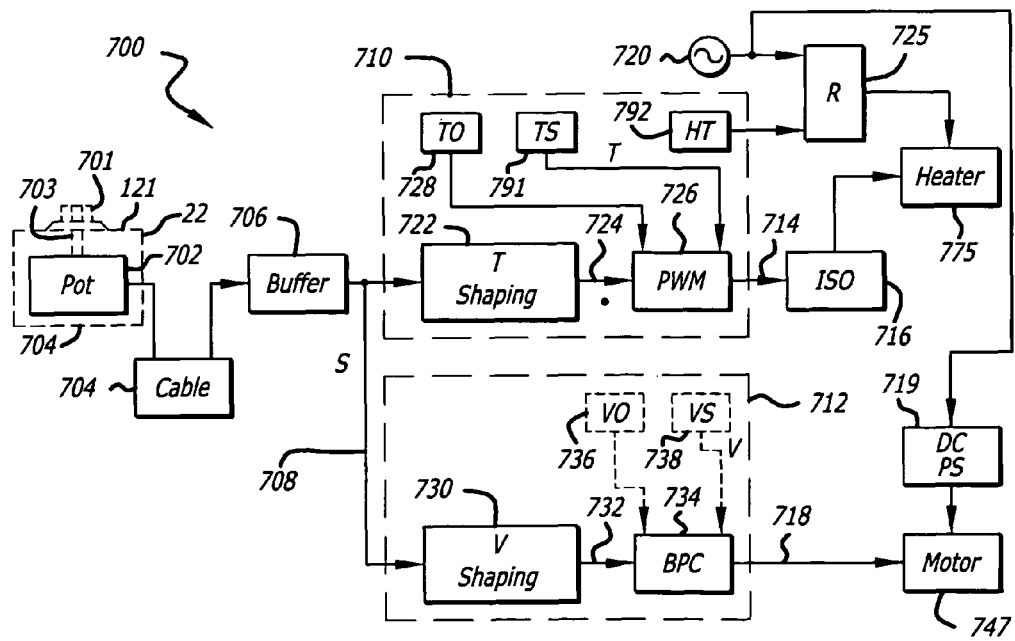
FIG. 7 is a schematic block diagram illustrating an exemplary embodiment of a controller suitable for causing a forced air warming unit to provide a stream of air exhibiting temperature and flow rate control characteristics such as those in FIG. 6.

FIG. 7 is a schematic block diagram illustrating representative functional architecture of an exemplary controller 700 for controlling the operations of the forced air warming unit 10 (FIG. 1). The elements of the controller 700 are distributed between the remote control 23 and the forced air warming unit 10. The controller elements in the remote control 23 include a manually-rotatable knob 701 mounted to the remote control 23 at the control surface 121. The knob 701 is connected by a shaft 703 to a potentiometer ("POT") 702 which generates a variable control signal S that is provided to the signal cable 24. The shaft 703 and potentiometer are mounted in the remote control 23. The remaining elements of the controller 700 are in the forced air warming unit 10. The signal cable 24 conducts the control signal to a buffer circuit 706. The control signal is buffered at 706 and provided to the line 708 and therefrom to a heater control circuit 710 and a motor control circuit 712 substantially as shown. The control signal S on the line 708 causes the heater control circuit 710 to produce a temperature level signal 714 that gates the current through the windings of the heater 775 by way of an optical-isolation circuit 716 in the usual manner. The control signal S on line 708 simultaneously causes the motor control circuit 712 to produce a motor speed control signal 718 that controls DC voltage from the DC power supply 719 to push current through the windings of the motor 747 sufficient to provide the desired air flow rate V in the usual manner. Power for the forced air warming unit 10 (FIG. 1) is accepted at the AC power plug 720 and transferred to the heater 775 by way of a power control relay circuit 725 and to the motor 747 by way of the DC power supply 719, in a manner similar to that discussed above in connection with FIG. 5.

With further reference to FIG. 7, the heater control circuit 710 includes a heater control shaping circuit 722 that accepts the control signal S on the line 708 and produces a heater control signal 724 in accordance with a temperature control characteristic such as, for example, the monotonic temperature control characteristic 602 (FIG. 6). A heater pulse-width-modulator (PWM) circuit 726 accepts the heater control signal 724 and produces the temperature level signal 714 by responsively varying the conductive duty-cycle in the usual manner. The current through heater 775 is switched on and off according to the duty cycle of the temperature level signal 714 (transferred by way of the opto-isolator 716) to achieve an air stream temperature T corresponding to the position of the potentiometer 702 as set by rotation of the knob 701 to a particular position. A temperature offset adjustment circuit 728 provides means for calibrating the PWM 726 to an operating point that achieves a desired temperature. The temperature sensor 791 feeds back a signal to the heater PWM 726 representing the actual air stream temperature T and the independent high temperature sensor 792 provides a fail-safe signal that causes the relay circuit 725 to disconnect power from heater plate 75 (FIGS. 2-4) whenever the actual air stream temperature T exceeds a predetermined threshold.

The motor control circuit 712 includes a flow rate (V) control shaping circuit 730 that accepts the control signal S on line 708 and produces a flow rate control signal 732 in accordance with a flow rate control characteristic such as, for example, the monotonic flow rate control characteristic 1004 (FIG. 6). A blower power control (BPC) circuit 734 accepts the flow rate control signal 732 and produces the motor speed signal 718 by responsively varying the effective direct current available to the motor in the usual manner to achieve an air stream flow rate V corresponding to the position of potentiometer 702 as set by rotation of the knob 701 to a particular position. Analogously to the heater control circuit 710, although not preferred, a flow rate offset adjustment circuit 736 could be added to provide means for calibrating the motor control circuit 734 to an operating point that achieves a desired flow rate V and a flow rate sensor 738 could be added to feed back a signal to the BPC 734 representing the actual air stream flow rate V.

Figure 8:
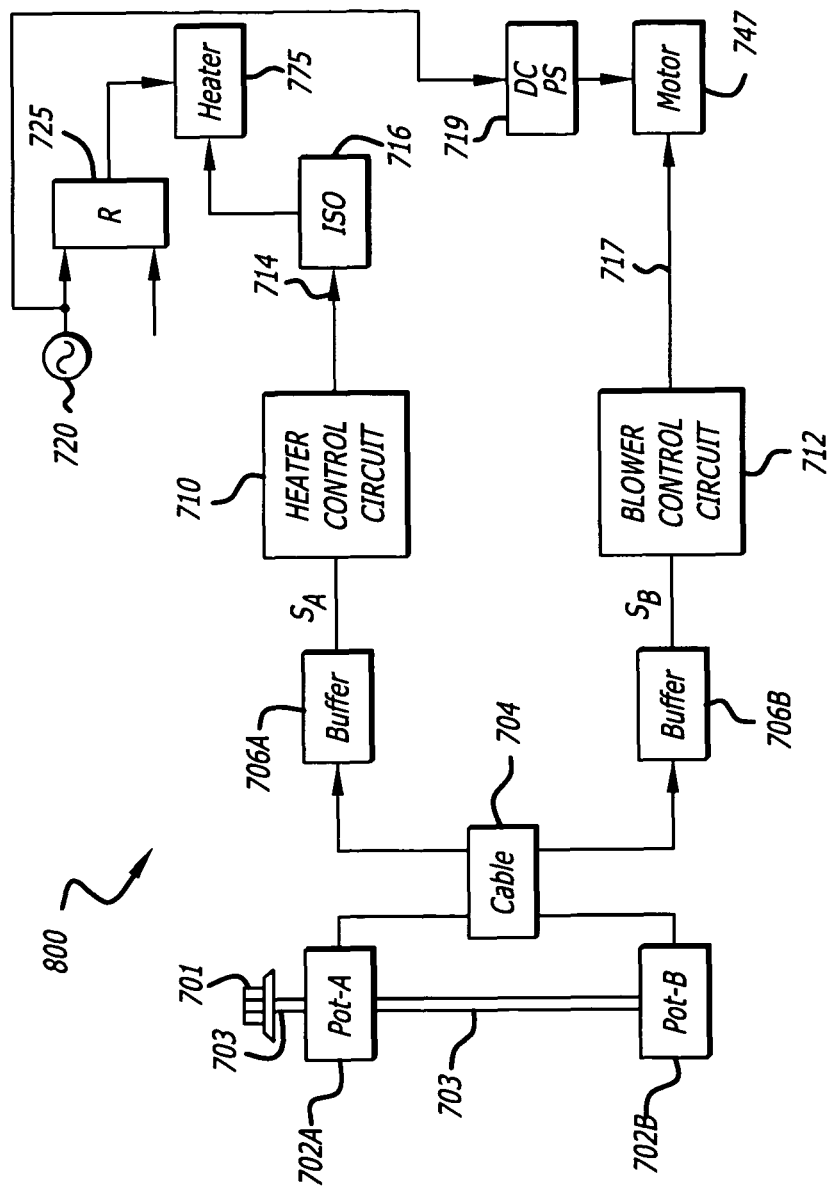
FIG. 8 is a schematic block diagram illustrating an alternative embodiment of a controller suitable for causing a forced air warming unit to provide a stream of air exhibiting temperature and flow rate control characteristics such as those in FIG. 6.

FIG. 8 is a schematic block diagram illustrating a functional architecture of another exemplary controller 800 for controlling the operations of the forced air warming unit 10 (FIG. 1). The elements of the controller 800 are distributed between the remote control 23 and the forced air warming unit 10. The controller elements in the remote control 23 include a manually-rotatable knob 701 rotatably mounted to the remote control 23 at the control surface 121 in the manner illustrated in FIG. 7. The knob 701 is connected to a first potentiometer 702A and a second potentiometer 702B by means of a shaft 703, thereby forming a dual ganged potentiometer in the usual manner. The shaft 703 and potentiometers 702A and 702B are mounted in the remote control 23; channels or conductors in the cable 24 connect the potentiometers 702A and 702B to the remaining elements of the controller 800, which are located in the forced air warming unit. The first potentiometer 702A affords a continuously-variable control signal $S_A$ that is provided through the signal cable 24 and a buffer circuit 706A to the line 708A and therefrom to a heater control circuit 710 substantially as shown. The second potentiometer 702B provides a continuously-variable control signal $S_B$ that is conducted through the signal cable 24 and a buffer circuit 706B to the line 708B and therefrom to a motor control circuit 712 substantially as shown. The control signal $S_A$ on the line 708A causes the heater control circuit 710 to produce heater control signal 714 (transferred by way of the opto-isolator 716) to achieve an air stream temperature T corresponding to the position of the potentiometer 702A as set by rotation of the knob 701 to a particular position. The control signal $S_B$ on line 708B simultaneously causes the motor control circuit 712 to produce the blower control signal 718 by responsively varying the effective direct current available to the blower in the usual manner to achieve an air stream flow rate V corresponding to the position of potentiometer 702B as set by rotation of the knob 701 to a particular position. Power for the forced air warming unit 10 (FIG. 1) is accepted at the AC power plug 720 and transferred to the heater 775 by way of a power control relay circuit 725 and to the blower motor 747 by way of the DC power supply 719, in a manner similar to that discussed above in connection with FIG. 6. Note that both T and V are controlled by means of independent signals $S_A$ and $S_B$ produced by positioning a single knob in a single user action. Operation of the controller 800 may be appreciated with reference to the above description of controller 700 (FIG. 7)

Figure 9:
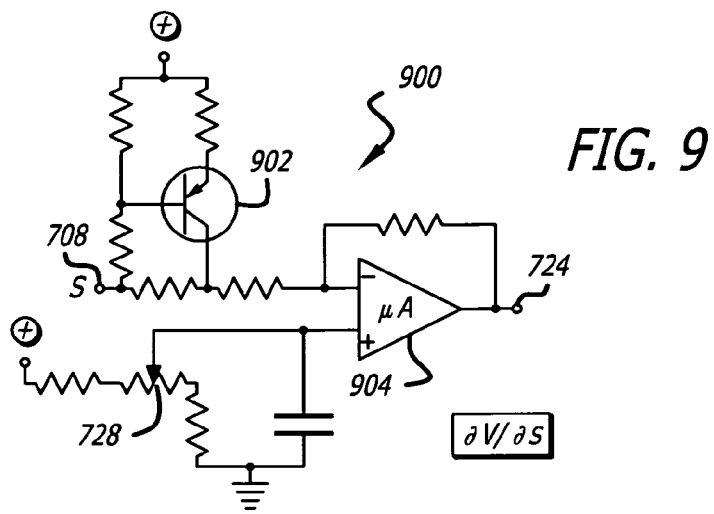
FIG. 9 is a schematic diagram illustrating an exemplary heater control shaping circuit embodiment suitable for use with the controller of FIG. 7.

FIG. 9 is explained with respect to the controller 700 with a single potentiometer, although it should be understood that it is also adaptable to the dual-potentiometer controller 800. FIG. 9 is a schematic diagram illustrating an exemplary heater control shaping circuit embodiment 900 for accepting the control signal S on line 708 and producing the temperature control signal 724 according to a temperature control characteristic approximated by the temperature control characteristic 1002 (FIG. 6). The transistor circuit 902 operates to gradually reduce the temperature control signal 724 as control signal S on the line 708 rises by virtue of the operational amplifier circuit 904, which subtracts from the temperature control signal 724 a portion of the control signal S on line 708 that varies with the magnitude of the control signal S in the usual manner. The temperature offset adjustment circuit 728 serves to bias the positive input of the operational amplifier circuit 904 for the purposes mentioned above in connection with FIGS. 7 and 8.

Figure 10:
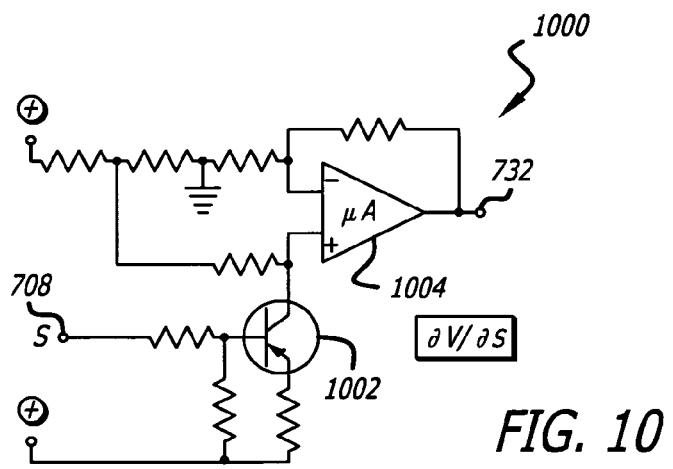
FIG. 10 is a schematic diagram illustrating an exemplary blower control shaping circuit embodiment suitable for use with the controller of FIG. 7.

FIG. 10 is explained with respect to the controller 700 with a single potentiometer, although it should be understood that it is also adaptable to the dual-potentiometer controller 800. FIG. 10 is a schematic diagram illustrating an exemplary blower control shaping circuit embodiment 1000 for accepting the control signal control signal S on the line 708 and producing the blower control signal 732 according to a flow rate control characteristic approximated by the flow rate control characteristic 604 (FIG. 6). The transistor circuit 1002 operates to gradually increase the flow rate control signal 732 as the control signal S on the line 708 rises by virtue of the operational amplifier circuit 1004, which adds to the flow rate control signal 732 a portion of the control signal S on the line 708 that varies with the magnitude of the control signal S in the usual manner.

Figure 11:
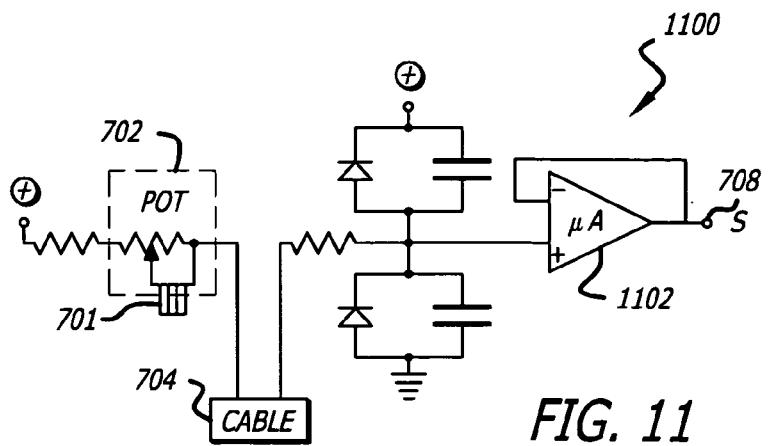
FIG. 11 is a schematic diagram illustrating an exemplary remote control circuit embodiment suitable for use with the controller of FIG. 7.

FIG. 11 is explained with respect to the controller 700 with a single potentiometer, although it should be understood that it is also adaptable to the dual-potentiometer controller 800. FIG. 11 is a schematic diagram illustrating an exemplary remote control circuit embodiment 1100, showing the potentiometer 702 coupled through the cable 724 to an operational amplifier buffer circuit 1102, which operates to isolate circuits and match impedances in the usual manner, thereby producing the control signal S on line 708.

Figure 12:
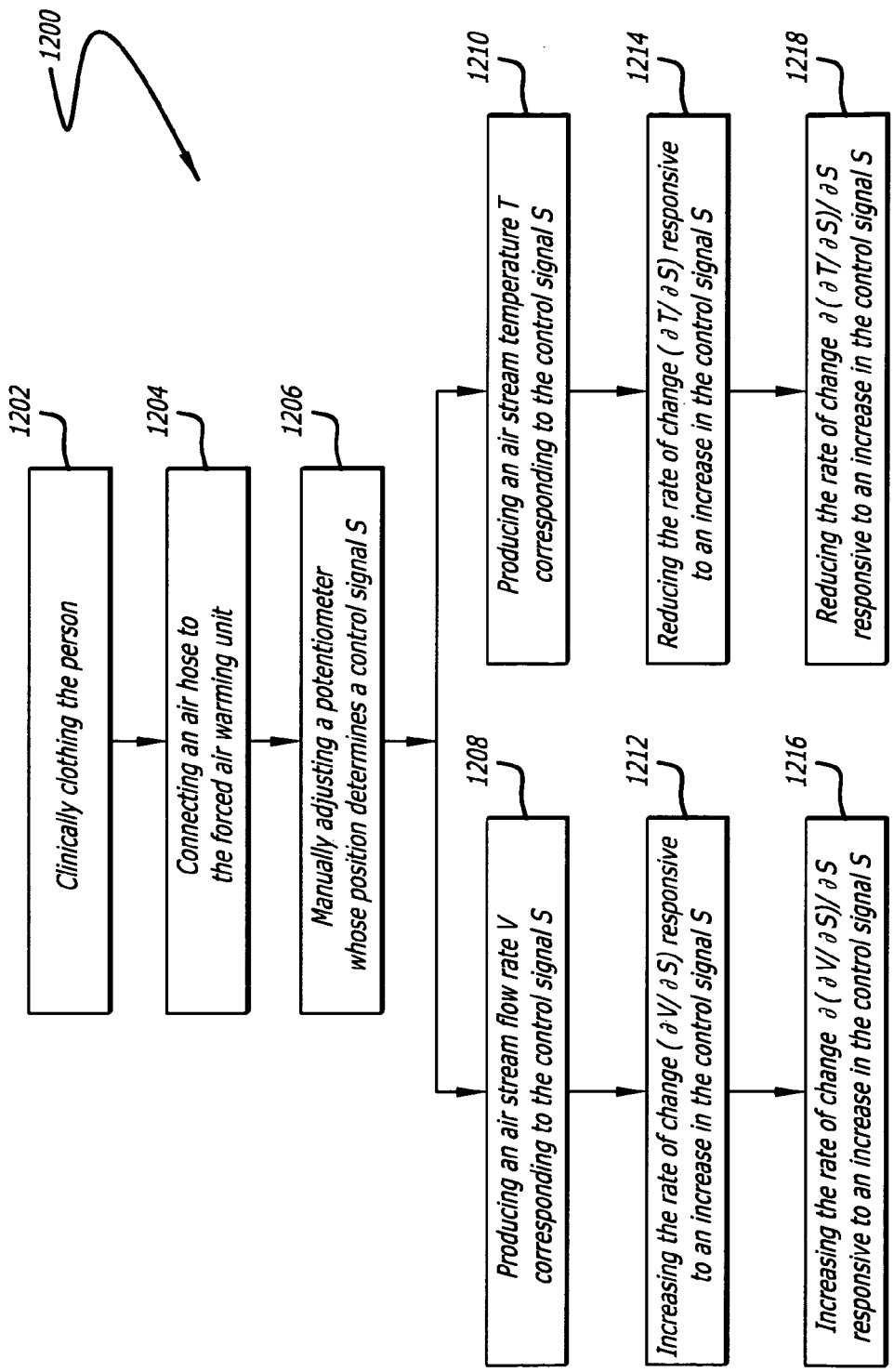
FIG. 12 is a schematic diagram illustrating an exemplary embodiment of a method for warming a person with regulation of temperature and air flow rate provided by a single act or operation of a single manually-operated element on a remote control apparatus.

FIG. 12 is a schematic diagram illustrating an exemplary method 1200 for warming a person. The first step 1202 is clothing the person in a clinical garment with a convective warming device mounted therein. In the next step 1204, an air hose is connected between the convective device and the forced air warming unit. In the third step 1206, a remote control unit is manually operated to change a control signal S. The following steps 1208 and 1210 are preferably performed simultaneously as shown. In step 1208, the forced air warming unit is controlled to provide a stream of thermally conditioned air having a flow rate V corresponding to the control signal S, and in step 1210 the forced air warming unit is controlled to provide a stream of thermally conditioned air having a temperature T corresponding to the control signal S. The method 1200 may also include either or both of the two preferably simultaneous steps 1212 and 1214. In step 1212, the rate of change ($\partial V/\partial S$) of the air stream flow rate V with respect to the control signal value S is increased responsive to an increase in the control signal S and in step 1214, the rate of change ($\partial T/\partial S$) of the air stream temperature T with respect to the control signal value S is reduced responsive to an increase in the control signal S. Finally, the method 1200 may also include either or both of the two preferably simultaneous steps 1216 and 1218. In step 1216, the rate of change $\partial(\partial V/\partial S)/\partial S$ with respect to the control signal S of the rate of change ($\partial V/\partial S$) of the air stream flow rate V with respect to the control signal S is increased responsive to an increase in the control signal S and in step 1218, the rate of change $\partial(\partial T/\partial S)/\partial S$ with respect to the control signal S of the rate of change ($\partial T/\partial S$) of the air stream temperature T with respect to the control signal S is reduced responsive to an increase in the control signal S.

Figure 13:
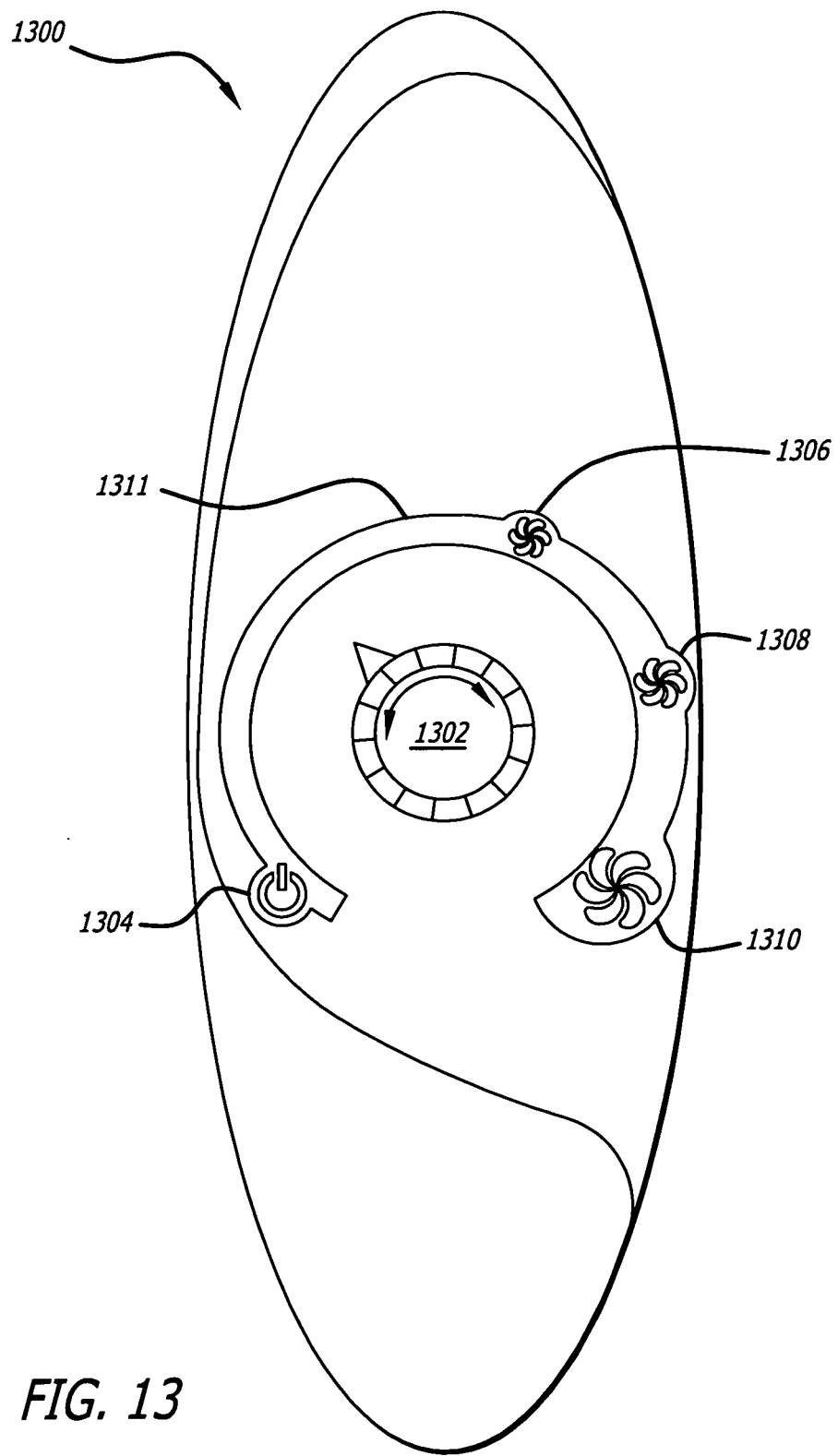
FIG. 13 is a diagram showing a control surface of an embodiment of a manually-operated remote control element used to control operations of a forced air warming unit.

FIG. 13 is a diagram illustrating a representative control surface embodiment 1300 for the remote control element 23. A single manually-operated control element is embodied as a knurled knob 1302 mounted to be rotatable with respect to the control surface 1300. The control surface 1300 includes an array of icons 1304-1310 painted or printed or otherwise affixed or embossed into the surface 1300. At least a portion of the array of icons represents a succession of discrete air stream speed/temperature conditions taken along the knob position axis of FIG. 6 for a representative set of T-V curves. Thus, the knob 1302 can be turned to indicate any of the several icons, or any point along the curve 1311 connecting the icons. The icon 1304 may indicate an "off" position, for example, and icons 1306-1310 may indicate fan speeds of varying magnitude, with corresponding temperatures. In the example illustrated, the icon 810 indicates a large fan (implying relatively higher fan speed) and the icon 806 indicates a small fan (implying relatively lower fan speed). A user may, with a single action, adjust the rotational position of knob 1302 to increase or decrease the "thermal comfort" setting, and obtain the physical results discussed above in connection with FIGS. 5-12.

The principles of single-act and single-element control of air stream T and V that are explained above are not limited to the illustrative knob and potentiometer combination. The single control element on a manually-operated remote control of such a system may be embodied in a knob, a selector, a multi-position switch, a key, a button, a slider, or any equivalent mechanism whose operation by a user causes a change in one or more characteristics of one or more control signals used to control, regulate, or adjust both T and V of the air stream. The single control element may operate in combination with one or more signal producing elements. Such signal producing elements include potentiometers, converters, look up tables, programmed arrays, or any equivalent mechanism. A control signal may be in analog or digital form, and may be converted from one form to the other. A control signal may be in electrical or optical form, and may be converted from one form to the other. The regulation in T and V produced in response to one or more control signals may be continuous, piece-wise continuous, or discontinuous.

The examples shown and discussed above are based on a tethered remote control apparatus with a manually-operated control knob. This is not meant to limit the possibilities of remote control/control circuitry interconnection. In other examples, the remote control may communicate with the control circuitry by means of a wire tether, or air-propagated signals, by electrical signals, IR signals, radio signals, by digitized or analog signals, or other means. In some instances, the remote control and the associated control circuitry may be combined into a base station comprising one small unit stationed near the patient.

Other configurations may combine any one or more of these embodiments, possibilities and examples as required by design considerations for different applications.

Still further modifications can be made without departing from the principles of warming control inherent in the apparatuses and methods described and illustrated herein. Accordingly, my invention is limited only by the following claims

I claim:

1. A combination for providing a stream of thermally conditioned air having a temperature T and a velocity V controlled by a user, comprising:
    a remote control;
    the remote control unit including a single manually-operated control element for adjusting a control signal S having a magnitude;
    a device for producing a stream of air having a velocity V and a temperature T;
    a temperature control unit in the device coupled to the remote control for establishing the temperature according to the control signal magnitude;
    a first control shaping circuit in the temperature control unit for reducing the rate of change ($\partial T/\partial S$) of the temperature with respect to the control signal responsive to an increase in the control signal magnitude; and
    a blower control circuit in the device coupled to the remote control and to the blower unit for establishing the velocity according to the control signal magnitude.

2. The combination of claim 1 further comprising:
    a second control shaping circuit in the blower control circuit for increasing the rate of change ($\partial V/\partial S$) of the velocity with respect to the control signal responsive to an increase in the control signal magnitude.

3. The combination of claim 1 further comprising:
    the single manually-operated control element being a manually-adjustable knob whose position determines the control signal magnitude.

4. The combination of claim 3, in which:
    the manually-adjustable knob is further for generating an on/off signal;
    further including means for turning the air stream on or off in response to the on/off signal.

5. The combination of claim 1 further comprising:
the single manually-operated control element being a manually-operable switch for changing the control signal magnitude.

6. The combination of claim 1 further comprising:
the single manually-operated control element being a manually-adjustable slider whose position determines the control signal magnitude.

7. The combination of claim 1 further comprising:
the single manually-operated control element being a manually-adjustable lever for changing the control signal magnitude.

8. The combination of claim 1 further comprising:
the single manually-operated control element being a single manually-adjustable knob coupled to two potentiometers each of whose position determines a control signal magnitude.

* * * * *